United States Patent [19]

Toscano

[11] Patent Number: 4,588,712

[45] Date of Patent: May 13, 1986

[54] (8S)-8-FLUOROERYTHROMYCIN DERIVATIVES, THE PROCESS FOR THE PREPARATION THEREOF AND THE PHARMACEUTICAL COMPOSITIONS CONTAINING THEM

[75] Inventor: Luciano Toscano, Naples, Italy

[73] Assignee: Pierrel S.p.A., Naples, Italy

[21] Appl. No.: 706,496

[22] Filed: Feb. 28, 1985

[30] Foreign Application Priority Data

Mar. 8, 1984 [IT] Italy ................. 19950 A/84

[51] Int. Cl.[4] ............... A61K 31/71; C07H 17/08
[52] U.S. Cl. ........................ 514/29; 536/7.2
[58] Field of Search ................ 536/7.2; 514/29

[56] References Cited

FOREIGN PATENT DOCUMENTS

| | | | |
|---|---|---|---|
| 0056291 | 7/1982 | European Pat. Off. | 536/7.2 |
| 0080763 | 6/1983 | European Pat. Off. | 536/7.2 |
| 0081305 | 6/1983 | European Pat. Off. | 536/7.2 |

*Primary Examiner*—Johnnie R. Brown
*Assistant Examiner*—Elli Peselev
*Attorney, Agent, or Firm*—Bucknam and Archer

[57] ABSTRACT

(8S)-8-fluoroerythromycin derivatives of formula

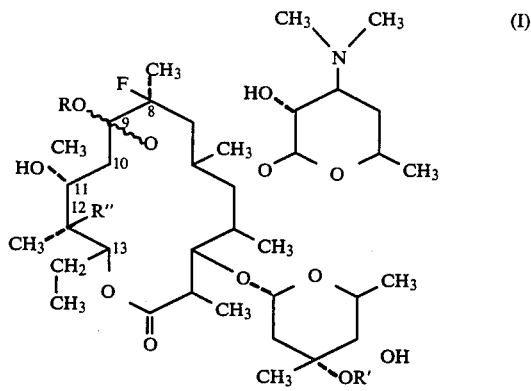

wherein
R is an optionally substituted alkyl, alkenyl or phenyl group
R' is hydrogen or methyl and
R" is hydrogen or hydroxy, may be prepared by fluorination of the corresponding 8,9-anhydroerythromycin 6,9-hemiketals with perchloryl fluoride in the presence of a compound ROH in strictly anhydrous conditions.

The new compounds as well as their pharmaceutically acceptable esters, salts and salt-esters may be employed as the active ingredients of pharmaceutical compositions for antibacterial use suitable for oral administration.

10 Claims, No Drawings

(8S)-8-FLUOROERYTHROMYCIN DERIVATIVES, THE PROCESS FOR THE PREPARATION THEREOF AND THE PHARMACEUTICAL COMPOSITIONS CONTAINING THEM

This invention relates to new (8S)-8-fluoroerythromycin derivatives which are useful as medicines.

(8S)-8-Fluoroerythromycins A, B, C and D as well as their esters, salts and salt-esters are known from EP-A-56291 where their preparation by mutational biosynthesis starting from the aglycones (8S)-8-fluoroerythronolide A and B, or the monoglycoside 3-O-mycarosyl-(8S)-8-fluoroerythronolide B is also described.

An alternative synthetic approach to these compounds is described in EP-A-80763, where their preparation through fluorination of the corresponding 8,9-anhydroerythromycin 6,9-hemiketal or 8,9-anhydroerythromycin 6,9-hemiketal N-oxide with a compound capable of generating electrophilic fluorine followed by reductive methylation or reduction of the obtained intermediate is taught.

It has now been discovered that new (8S)-8-fluoroerythromycin derivatives can be obtained by fluorination of an 8,9-anhydroerythromycin 6,9-hemiketal or its N-oxide in suitable conditions. The new compounds which share a fair in vitro antibacterial activity, upon oral administration, are capable of releasing the known highly active (8S)-8-fluoroerythromycins.

More particularly this invention relates to new (8S)-8-fluoroerythromycin 6,9-hemiketal derivatives of the formula

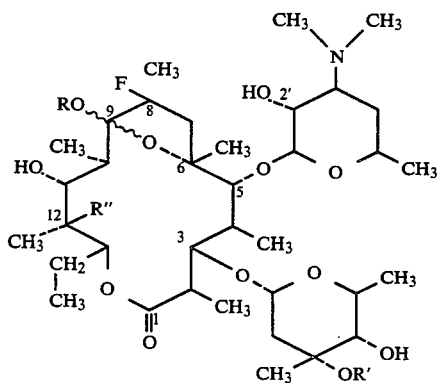

wherein
R is $(C_1-C_{10})$ alkyl or $(C_3-C_{10})$ alkenyl optionally substituted with a group selected from lower alkoxy, cycloalkoxy, phenyl, substituted phenyl and substituted amino of formula

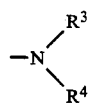

wherein $R^3$ and $R^4$, each independently, represent lower alkyl or benzyl or $R^3$ and $R^4$ taken together with the adjacent nitrogen atom may represent a pyrrolidine, piperidine, piperazine or morpholine moiety;
or
R is phenyl or substituted phenyl;

R' is hydrogen or methyl; and
R" is hydrogen or hydroxy.

The term "$(C_1-C )$alkyl" designates a straight or branched alkyl radical containing from 1 to 10 carbon atoms, such as for instance methyl, ethyl, n-propyl, isopropyl, n-butyl, sec-butyl, pentyl, isopentyl, t-pentyl, n-hexyl, n-heptyl, 3-propyl-butyl, 3-propyl-heptyl, n-nonyl, and the like while the term "$(C_3-C_{10})$alkenyl" identifies alkenyl radicals containing 3 to 10 carbon atoms and one or more double bonds such as for instance allyl, crotyl, 2,4-hexadienyl and the like. As the "lower alkoxy" group, there may be exemplified as straight or branched $(C_1-C_4)$alkoxy group such as methoxy, ethoxy, propoxy, n-butoxy or t-butoxy, and, as the "cycloalkoxy" group, there may be exemplified a $(C_5-C_8)$cycloalkoxy group such as cyclopentyloxy, cyclohexyloxy, cycloheptyloxy or cyclooctyloxy.

As used herein the term "substituted phenyl" designates a phenyl radical substituted in any of its positions with 1, 2, or 3 groups independently selected from $(C_1-C_4)$alkyl, $(C_1-C_4)$alkoxy, $(C_1-C_4)$alkylthio, $(C_3-C_4)$alkenyl, halo and nitro. Halo generically indicates any of fluoro, chloro, bromo or iodo.

A preferred group of compounds of the present invention comprises those compounds of formula (I) wherein R is as defined above, R' is methyl and R" is hydroxy.

A most preferred group of compounds of the present invention comprises those compounds of formula (I) wherein R is $(C_1-C_{10})$ alkyl optionally substituted as defined above, R' is methyl and R" is hydroxy.

As for the stereochemical configuration of the —OR group at C-9, the wavy line indicates that the substituent may be either α- or β-positioned. Both the single isomers bearing the —OR group in a fixed configuration as well as any mixture thereof do fall within the scope of the present invention.

The compounds of the present invention are prepared starting from the corresponding 8,9-anhydroerythromycin 6,9-hemiketals or their N-oxides of the formula

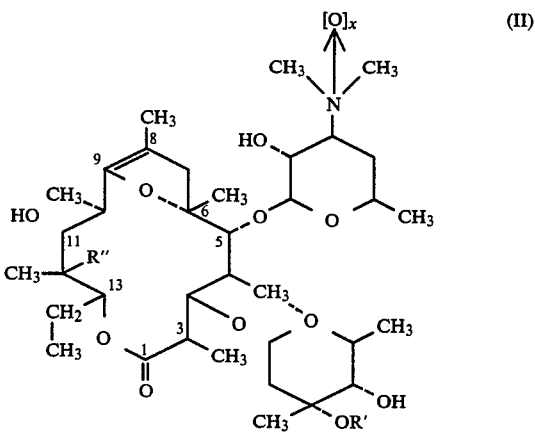

wherein R' and R" are as defined above and x is 0 or 1, by reaction with perchloryl fluoride in the presence of a compound of formula ROH, wherein R is as defined above, in strictly anhydrous conditions. Thus, the fluorination reaction is carried out by slowly bubbling perchloryl fluoride into a solution of the 8,9-anhydroerythromycin substrate (II) and an at least equimolar amount of a suitably selected alcohol of formula ROH. Whenever possible, the reaction is preferably carried out in an excess of the reacting alcohol, the excess alcohol serving as the reaction solvent as well.

Alternatively, a polar, aprotic solvent which is able to solubilize both reagents and does not negatively interfere with the reaction course, may be employed as the reaction solvent or cosolvent. Useful solvents include aliphatic and aromatic halogenated hydrocarbons such as chloroform, methylene chloride, and chlorobenzene, pyridine, collidines, picolines, dioxane, tetrahydrofuran and the like solvents. The reaction is conveniently carried out at low temperature, typically between $-10°$ C. and room temperature. Preferably however the reaction temperature is kept between $-10°$ C. and $+10°$ C.

The reaction course is easily monitored by HPLC by collecting samples of the reaction mixture at different times.

When disappearance of the starting erythromycin substrate is observed, perchloryl fluoride bubbling is discontinued, the excess perchloryl fluoride is removed by passing an inert gas stream through the reaction mixture and the desired product is recovered and purified by conventional procedures.

In particular, for instance, the reaction mixture is diluted with water and the pH is made slightly basic by the addition of a strong alkali diluted solution. The organic solvent is then evaporated off and the aqueous phase is extracted with a suitably selected polar and aprotic organic solvent such as for instance ethyl acetate, isopropyl acetone, chloroform, methylene chloride, dichloroethane and the like. The organic solution is then washed with water, dried and concentrated to dryness yielding the desired product as a raw residue.

Purification of the thus obtained residue is conveniently carried out by column chromatography and/or crystallization from suitable solvents. Useful crystallization solvents are for instance aliphatic ketones such as acetone, ethyl acetone, etc., cyclic or alicyclic aliphatic hydrocarbons such as pentane, hexane, heptane, octane, cyclohexane, cycloheptane and their mixtures.

The starting 8,9-Anhydroerythromycin 6,9-hemiketals and the corresponding N-oxides are known compounds and can be prepared according to methods known in literature (see for instance P. Kurath et al. Experientia 27, (1971), 362). When the fluorination reaction of the present invention is carried out starting from the N-oxides, the N-oxide is removed at the end of the reaction by conventional reduction procedures such as those described in EP-A-80763 which are incorporated herein by reference. The compounds of the present invention show a fair antimicrobical activity when tested in vitro in comparison with flurythromycin. More particularly they show the same spectrum of activity as flurythromycin, mainly against gram-positive bacteria including *S.Aureus, Str. faecalis, Str. pneumoniae, Micrococcus luteus, Corynebacterium diphteriae* etc., but they are active to a lesser extent as compared to flurythromycin.

However the compounds of the present invention which are stable at neutral and basic pH, readily decompose in mild acidic conditions (in conditions which simulate the gastric juice) to give the corresponding (8S)-8-fluoroerythromycins, antibiotic substances of remarkable therapeutical interest already known in literature (see again EP-A-56291). In particular, experiments carried out at room temperature, in aqueous solutions brought to pH 2 by the addition of HCl, show that generally the new (8S)-8-fluoroerythromycin derivatives are converted into the corresponding (8S)-8-fluoroeythromycins by more than 50% in the first 10 minutes, while an almost complete conversion is achieved within $\frac{1}{2}$ hour. More particularly, quantitative results for flurythromycin 6,9(R)-methylketal ((I): R=methyl; R'=methyl; R"=hydroxy) and flurythromycin 6,9-ethylketal ((I): R=ethyl; R'=methyl; R"=hydroxy) show that a 95% conversion is obtained in 26 and 10 minutes respectively.

Owing to the ease of conversion into the corresponding (8S)-8-fluoroerythromycins in mild acidic environment, the compounds of the present invention may be employed both as intermediates in the manufacture of the corresponding 8-fluoroerythromycins and as antibiotic substances with the same antibiotic spectrum as the corresponding (8S)-8-fluoroerythromycins, suitable for oral administration.

For this latter use, the compounds of the present invention can be employed as such or as the corresponding pharmaceutically acceptable esters, salts and salt-esters, in the preparation of pharmaceutical compositions suitable for oral administration.

The mono-esters of the new compounds of formula (I), such for instance the acetate, propionate, butyrate, ethylsuccinate, valerate, stearate and the like do fall within the scope of the present invention. These mono-esters may be easily prepared according to methods known in literature, analogous to those employed for the preparation of erythromycin esters, which comprise reacting the (8S)-8-fluoroerythromycin derivative of formula (I) with about one molecular equivalent of an acylating agent which can be the acid halide or the anhydride of a suitably selected acid in the presence of at least a molecularly equivalent amount of a base, such as an alkali metal hydroxide or carbonate which acts as acceptor of the acid which forms during the reaction, and in the presence of a polar and aprotic organic solvent which does not negatively interfere with the esterification reaction.

Also within the scope of the present invention are the 11,12-carbonates of the new (8S)-8-fluoroerythromycin derivatives (I) and of the corresponding mono-esters. The carbonates are readily obtained by reacting the suitably selected (8S)-8-fluoroerythromycin derivative (I) or its mono-ester with a strong excess ethylene carbonate in the presence of an alkaline-reacting substance and an inert solvent. Alternatively 11,12-carbonate derivatives of the compounds of formula (I) can be prepared by fluorination of 8,9-anhydroerythromycin 6,9-hemiketal 11,12 carbonate or its mono-ester in the presence of an alcohol ROH in strictly anhydrous conditions.

Both the new antibiotic substances of formula (I) and the corresponding mono-esters and carbonates owing to the presence of a salifiable basic group are capable of forming acid addition salts. However, as the compounds of formula (I) as well as their esters, are unstable in acidic conditions, only their addition salts with weak organic acids can be prepared such as the lactobionate, glucoheptonate, stearate, etc. These acid addition salts are prepared according to procedures customarily employed in the preparation of erythromycin and flurythromycin acid addition salts.

Therapeutic compositions according to the present invention for oral administration embodying the new erythromycin derivatives of formula (I), their esters, salts or salt-esters, are prepared by compounding a compound of formula (I) or an ester, salt or salt-ester thereof with a conventional vehicle, excipients, binders, preservatives, stabilizers, flavoring agents or the like as called for by acceptable pharmaceutical practice. Also, the compounds used in this invention can be formulated with other pharmaceutically active compounds. Suitable dosage forms for oral administration include capsules, tablets, chewable tablets, elixirs and syrups.

Said dosage forms will preferably contain from 20 to 600 mg of a compound of the invention per dosage unit.

More particularly the tablets may contain inert excipients merely to increase the formulation bulk such as lactose, starch, mannitol, sorbitol, inositol, kaolin and the like; binders, used to impart cohesive qualities to the tablet formulation such as, for instance, starch, gelatin, lactose, polyvinylpyrrolidone, carboxymethylcellulose, hydroxypropylcellulose etc., lubricants to improve the flowability of the powder to be compressed and improve therefore the compression step, such as talc, magnesium stearate, calcium stearate etc., disintegrators to facilitate disintegration of the tablet after administration, such as corn starch, potato starch, methylcellulose, bentonite etc., natural and artificial sweeteners, flavoring and coloring agents.

Chewable tablets may contain a sufficient amount of diluents such as lactose, mannitol and sorbitol, to impart properties to the tablet that permit disintegration in the mouth by chewing. Capsules may be filled with the active ingredient either alone or admixed with an inert excipient as seen above.

Oral liquid preparations may be in the form of suspensions or solutions or they may be presented as a dry product for recostitution with water or other suitable aqueous vehicle before use.

These liquid preparations may contain conventional additives such as suspending agents, for example, sorbitol, methyl cellulose, glucose/sugar syrup, gelatin, hydroxyethylcellulose, or carboxymethylcellulose, stabilizers, flavoring and sweetening agents.

The following examples described in details some representative compounds of the present invention, the method for their preparation and some pharmaceutical compositions containing them. It is to be understood that the purpose of this recitation is to further illustrate the invention and not to impose any additional limitation.

EXAMPLE 1

(8S)-8-fluoroerythromycin A 6,9(R)-methylketal ((I): R=—CH$_3$; R'=—CH$_3$; R"=—OH).

8,9-Anhydroerythromycin A 6,9-hemiketal ((II): R'=—CH$_3$; R"=—OH) (1.43 g, 2 mmol) is dissolved in absolute methanol (60 ml).

Perchloryl fluoride is then slowly bubbled in the solution cooled to ±5° C. until HPLC monitoring shows the disappearance of the starting compound. Nitrogen is then bubbled to remove the excess perchloryl fluoride, water (30 ml) is added and the pH is brought to 8–9 by addition of 5% NaOH. Methanol is removed under vacuum at 40°–45° C. and the aqueous phase is extracted with methylene chloride.

The organic extract is then washed with water up to neutral reaction, dried over Na$_2$SO$_4$ and concentrated to dryness under vacuum. The raw product thus obtained is purified by silica-gel column chromatography [N. L. Oleinick et al., J. Biol. Chem., 244, 727 (1969)] yielding (8S)-8-fluoroerythromycin A 6,9-methylketal (0.92 g, 60% yield) with the following characteristics: amorphous melting at 105°–10° C.

$[\alpha]_D^{20}$ −57.5° (c=1, methanol)

IR absorption bands (KBr): 3460, 1720, 1450, 1370, 1300, 1270, 1260, 1235, 1160 cm$^{-1}$.

NMR peaks (p$_y$—d$_5$) (δ): 2.20 (NMe$_2$), 3.35 (C$_{3''}$—OMe), 3.65 (C$_9$—OMe)

Elemental analysis: Calculated for C$_{38}$H$_{68}$FNO$_{13}$: %C 59.59; %H 8.95; %F 2.48; %N 1.83. Found: %C 59.64; %H 8.90; %F 2.38; %N 1.77.

From NMR correlation studies between known fluoroerythromycins having well defined sterical configurations at C-8 and C-9 and the obtained compound, it is inferred that the chiral center at C-9 has the R absolute configuration.

EXAMPLE 2

(8S)-8-fluoroerythromycin A 6,9(R)-ethylketal((I): R=—CH$_2$CH$_3$; R'=—CH$_3$; R"=—OH)

The compound of the title is obtained, by following the procedure described in example 1, through fluorination of 8,9-anhydroerythromycin A 6,9-hemiketal with perchloryl fluoride in absolute ethanol, and is purified by silica gel column chromatography giving a compound (63% yield) with the following characteristics: amorphous melting at 100°–10° C.

$[\alpha]_D^{20}$ −53.8°(C=1, methanol)

IR absorption bands (KBr): 3465, 1720, 1450, 1370, 1300, 1270, 1235, 1160 cm$^{-1}$.

Elemental analysis: Calculated for C$_{39}$H$_{70}$FNO$_{13}$: %C 60.06; %H 9.05; %F 2.44; %N 1.72. Found: %C 60.79; %H 9.02; %F 2.42; %N 1.72.

EXAMPLE 3

(8S)-8-fluoroerythromycin A 6,9(R)-butylketal ((I): R=—(CH$_2$)$_3$—CH$_3$; R'=—CH$_3$; R"=—OH).

By following the procedure described in example 1, 8,9-anhydroerythromycin A 6,9-hemiketal is converted into (8S)-8-fluoroerythromycin A 6,9(R)-butylketal through fluorination with perchloryl fluoride in absolute butanol. Upon purification of the raw material by silica gel column chromatography followed by crystallization from n-hexane, an amorphous product (55% yield) is obtained with the following characteristics: amorphous melting at 105°–10° C.

$[\alpha]_D^{20}$ −55.2°(C=1, methanol)

IR absorption bands (KBr): 3460, 1725, 1450, 1370, 1340, 1320, 1160 cm$^{-1}$.

Elemental analysis: Calculated for C$_{41}$H$_{74}$FNO$_{13}$: %C 60.95; %H 9.23; %F 2.35; %N 1.73 Found: %C 60.98; %H 9.20; %F 2.33; %N 1.70.

EXAMPLE 4

(8S)-8-fluoroerythromycin A 6,9(R)-isopropylketal ((I):

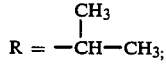

R'——CH$_3$; R"=—OH).

By following the procedure described in example 1, 8,9-anhydroerythromycin A 6,9-hemiketal is converted into (8S)-8-fluoroerythromycin A 6,9(R)-isopropylketal through fluorination with perchloryl fluoride in absolute isopropanol.

Upon purification of the raw product by silica gel column chromatography, an amorphous product (43% yield) is obtained with the following chacteristics: amorphous melting at 95°–100° C.

$[\alpha]_D^{20} - 39.2°$ (C=1, methanol)

I.R. absorption bands (KBr): 3480, 1725, 1450, 1370, 1335, 1320, 1270, 1160 cm$^{-1}$.

Elemental anlysis: Calculated for $C_{40}H_{72}FNO_{13}$: %C 60.51; %H 9.14; %F 2.39; %N 1.70 Found: %C 60.65; %H9.21; %F 2.33, %N 1.69.

EXAMPLE 5

(8S)-8-fluoroerythromycin A 6,9(R)-methylketal 2'-propionate.

Propionic anhydride (1.95 g, 0.015 mol) is added to a solution of (8S)-8-fluoroerythromycin A 6,9(R)-methylketal (7.65 g, 0.010 mol) in anhydrous acetone (76.5 ml). The reaction mixture is stirred at room temperature for 6 hours, then poured into ice-water and extracted with chloroform (three portions). The organic extracts are combined, dried over $Na_2SO_4$ and concentrated to dryness under vacuum to yield a raw residue ($\simeq$10 g). Upon crystallization from ethyl ether/n-hexane the compound of the title (5.5 g) is obtained with the following chemico-physical characteristics: m.p. 101°-3° C.;

$[\alpha]_D^{20} - 50.75°$(C=1, acetone)

IR (KBr) 3480, 1735, 1460, 1375, 1170 cm$^{-1}$.

Elemental analysis: Calculated for $C_{41}H_{72}FNO_{14}$: %C 59.91 %H 8.83; %F 2.31; %N 1.70. Found: %C 60.07; %H 8.79; %F 2.37; %N 1.65

EXAMPLE 6

(8S)-8-fluoroerythromycin A 6,9(R)-methylketal 2'-propionate thiosuccinate salt.

Thio-succinic acid (3 g, 0.020 mol) is added to a stirred solution of the compound of example 5 (19.45 g, 0.020 mol) in acetone (25 ml). The reaction mixture is stirred until a solution is obtained (about 30 minutes), then distilled water (12.5 ml) is added thereto. As soon as the product begins to crystallize out, an additional amount of water (125 ml) is added and the mixture is stirred at room temperature for 30 minutes and filtered under vacuum. The crystalline product which is obtained is dried until constant weight, under high vacuum at 30° C. (8S)-8-fluoroerythromycin A 6,9(R)-methylketal 2'-propionate thiosuccinate salt(125 g) is obtained with the following chemico-physcial characteristics:

m.p. 160°-2° C.

$[\alpha]_D^{20} - 47.8°$ (C=1, acetone)

IR (KBr) 3460, 1730, 1590, 1460, 1375, 1170 cm$^{-1}$.

Elemental analysis: Calculated for $C_{45}H_{78}FNO_{18}S$: %C 55.60; %H 8.09; %F 1.95; %N 1.44; %S 3.30. Found: %C 55.73; %H 8.15; %F 1.89; %N 1.48; %S 3.41.

EXAMPLE 7

(8S)-8-fluoroerythromycin A 6,9(R)-methylketal stearate salt.

A solution of stearic acid (2.85 g, 0.010 mol) in anhydrous acetone (100 ml) is added to a solution of (8S)-8-fluoroerythromycin A 6,9(R)-methylketal (7.65 g, 0.010 mol) in anhydrous acetone (76.5 ml). The obtained solution is allowed to stand at room temperature overnight. The precipitate which forms is recovered by filtration and dried under vacuum at room temperature yielding the compound of the title (8.85 g) with the following chemico-phisical characteristics:

melting point: 86°-7° C.

$[\alpha]_D^{20} - 41.4°$ (C=1, acetone)

IR (KBr): 3460 (broad), 1725, 1560 (broad), 1460, 1375, 1165 cm$^{-1}$.

Elemental analysis: Calculated for $C_{56}H_{104}FNO_{15}$: %C 64.03; %H 9.98; %F 1.81; %N 1.33 Found: %C 63.85; %H 9.811 %F 1.74; %N 1.37.

EXAMPLE 8

(8S)-8-fluoroerythromycin A 6,9(R)-methylketal 11,12-carbonate.

A solution of ethylene carbonate (7.045 g, 0.080 mol) in anhydrous benzene is gradually added over 60 minutes to a mixture of (8S)-8-fluoroerythromycin A 6,9(R)-methylketal (7.65 g, 0.010 mol) and $K_2CO_3$ (3.76 g) in anhydrous benzene (20 ml) stirred at 95° C.

When the addition is complete, the reaction mixture is refluxed for 15 minutes and cooled to room temperature, then it is washed with water, dried over anhydrous $Na_2SO_4$ and dried under vacuum.

The raw product thus obtained is crystallized from acetone/n-hexane to yield the compound of the title with the following chemico-physical characteristics: m.p. 128°-32° C.

$[\alpha]_D^{20} - 55°$(C=1, methanol)

IR (KBr): 3460 (broad), 1810, 1735, 1460, 1380, 1230, 1170 cm$^{-1}$.

NMR (CDCl$_3$) ($\delta$): 2.43 (s, 6, NMe$_2$), 3.26 (s, 3, 3''-OCH$_3$), 3.40 (s, 3, 9R—OCH$_3$).

Elemental analysis: Calculated for $C_{39}H_{66}FNO_{14}$: %C 59.15; %H 8.40; %F 2.40; %N 1.77. Found: %C 59.05; %H 8.31; %F 2.34; %N 1.93.

EXAMPLE 9

(8S)-8-fluoroerythromycin A 6,9(R)-methylketal 11,12-carbonate. The compound of the title (2.8 g) has also been obtained by following the method described in example 1 but starting from 8,9-anhydroerythromycin A 6,9-hemiketal 11,12-carbonate (7.4 g, 0.010 mol).

EXAMPLE 10

(8S)-8-fluoroerythromycin A 6,9(R)-methylketal 11,12-carbonate 2'-propionate.

By following the general procedure described in example 5 but starting from (8S)-8-fluoroerythromycin A 6,9(R)-methylketal 11,12-carbonate (7.920 g, 0.010 mol) as prepared in examples 8 or 9, the compound of the title (6.335 g) is obtained characterized by the following chemico-physical properties:

m.p. 201°-2° C.

$[\alpha]_D^{20} - 60.75°$(C=1, acetone)

IR (KBr): 3480, 1810, 1740, 1460, 1390, 1370, 1360, 1330, 1310, 1225, 1170 cm$^{-1}$.

Elemental analysis: Calculated for $C_{42}H_{70}FNO_{15}$: %C 59.49; %H 8.32; %F 2.24; %N 1.65. Found: %C 59.23; %H 8.28; %F 2.21; %N 1.73.

EXAMPLE 11

Preparation of (8S)-8-fluoroerythromycin A 6,9(R)-methylketal. 8,9-Anhydroerythromycin A 6,9-hemiketal N-oxide (7.3 g, 0.010 mol) is dissolved in absolute methanol (300 ml) and cooled to $\pm$5° C.

Perchloryl fluoride is then slowly bubbled in the solution until HPLC monitoring show the disappearance of the starting compound.

Nitrogen is then passed through the reaction mixture to remove the excess perchloryl fluoride. The solution is hydrogenated (1 atm. of H$_2$, 28° C.) in the presence of 5% Pd/C (2.65 g) for 2.5 hours.

The catalyst is removed by filtration and washed several times with methanol. The combined filtrates were evaporated to give 7.75 g of a raw residue which is crystallized from acetone/n-hexane yielding 6.2 g of (8S)-8-fluoroerythromicin A 6,9(R)-methylketal with same chemico-physical properties of the compound obtained in example 1.

EXAMPLE 12

Preparation of tablets

A granulate is prepared by means of the wet granulation techniques starting from the following listed ingredients: (8S)-8-fluoroerythromycin A 6,9(R)-methylketal(261 g), corn starch (80 g) and lactose (40 g). The granulate is then dried and blended with talc (16 g) and magnesium stearate (3 g). The mixture is then compressed yielding 1000 tablets weighing 400 mg each, containing 261 mg of (8S)-8-fluoroerythromycin A 6,9(R)-methylketal equivalent to 250 mg of flurythromycin) per unit.

EXAMPLE 13

Preparation of capsules (8S)-8-fluoroerythromycin A 6,9(R)-ethylketal (425 g) and magnesium stearate (12 g) are thoroughly mixed and the obtained blended mixture is used to fill 1000 hard gelatin capsules.

Each capsule will contain 437 mg of the blended mixture, 425 mg of which of (8S)-8-fluoroerythromycin A 6,9(R)-ethylketal (equivalent to 400 mg of flurythromycin).

EXAMPLE 14

Preparation of a suspension for extemporaneous preparation

A mixture of (8S)-8-fluoroerythromycin 6,9(R)-isopropylketal (5.4 g), flavouring agents (5 g), sodium carboxymethylcellulose (0.1 g), p-hydroxybenzoic acid methyl ester (0.3 g) and powdered sugar to a total weight of 250 g, is poured into a 250-ml calibrated bottle. Just before use, the bottle is filled with water to give a 250-ml suspension containing 21.6 mg of (8S)-8-fluoroerythromycin A 6,9(R)-isopropylketal (equivalent to 20 mg of flurythromycin) per ml.

I claim:

1. A compound of formula (1)

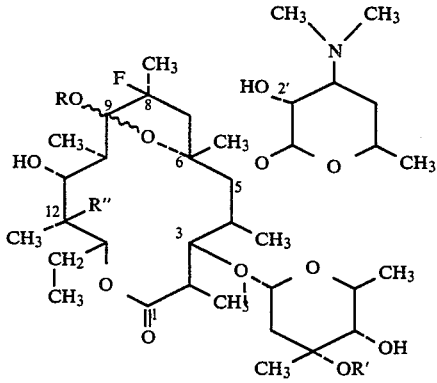

(I)

wherein R is an unsubstituted $C_1$–$C_{10}$ alkyl or unsubstituted $C_3$–$C_{10}$ alkenyl or R is $C_1$–$C_{10}$ alkyl or $C_3$–$C_{10}$ alkenyl substituted with a radical which a member selected the group consisting of lower alkoxy, cycloalkoxy, phenyl, substituted phenyl and substituted amino of formula $$-N\begin{array}{c}R^3\\R^4\end{array}$$

wherein $R^3$ and $R^4$, each independently, are lower alkyl or benzyl or $R^3$ and $R^4$ together with the adjacent nitrogen atom form a pyrrolidine, piperidine, piperazine or morpholine ring; or R is phenyl or substituted phenyl;
R' is hydrogen or methyl; and
R" is hydrogen or hydroxy,
pharmaceutically acceptable esters, organic acid addition salts, and salt-esters thereof.

2. A compound according to claim 1 wherein R' is methyl and R" is hydroxy.

3. A compound according to claim 2 wherein R is said substituted ($C_1$–$C_{10}$)alkyl.

4. A compound according to claim 1 wherein the absolute configuration at C-9 is R.

5. A compound of claim 1 which is the (8S)-8-fluoroerythromycin A 6,9(R)-methylketal, its pharmaceutically acceptable esters, salts and salt-esters.

6. A compound of claim 1 which is the (8S)-8-fluoroerythromycin A 6,9(R)-ethylketal, its pharmaceutically acceptable esters, salts and salt-esters.

7. A compound of claim 1 which is the (8S)-8-fluoero-erythromycin A 6,9(R)-isopropylketal, its pharmaceutically acceptable esters, salts and salt-esters.

8. A compound of claim 1 which is the (8S)-8-fluoroerythromycin A 6,9(R)-butylketal, its pharmaceutically acceptable esters, salts and salt-esters.

9. A process for preparing a compound according to claim 1 which consists of fluorinating a solution of a 8,9-anhydroerythromycin 6,9-hemiketal or the corresponding N-oxide of formula (II)

wherein R' and R" are as defined in claim 1 and x is 0 or 1 with perchloryl fluoride in the presence of at least an equimolar amount of a compound of formula ROH wherein R is as defined in claim, 1 in strict anhydrous conditions, and reducing the obtained intermediate when x is 1, and converting the obtained compound into a pharmaceutically acceptable ester, salt or salt-ester.

10. An antibiotic pharmaceutical composition for oral administration comprising a therapeutically effective amount of a compound of claim 1 and a pharmaceutical carrier therefor.

* * * * *